US008535349B2

(12) United States Patent
Chen et al.

(10) Patent No.: US 8,535,349 B2
(45) Date of Patent: Sep. 17, 2013

(54) FISTULA GRAFTS HAVING A DEFLECTABLE GRAFT BODY PORTION

(75) Inventors: Steve Chen, Westfield, IN (US); Jeremy Metz, Indianapolis, IN (US); F. Joseph Obermiller, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1182 days.

(21) Appl. No.: 12/166,015

(22) Filed: Jul. 1, 2008

(65) Prior Publication Data
US 2009/0012558 A1 Jan. 8, 2009

Related U.S. Application Data

(60) Provisional application No. 60/947,573, filed on Jul. 2, 2007.

(51) Int. Cl.
*A61B 17/04* (2006.01)
(52) U.S. Cl.
USPC ........... 606/213; 606/214; 606/215; 606/216; 606/228; 623/11.11
(58) Field of Classification Search
USPC ..................... 606/213, 214, 215; 600/30, 31, 600/32; 623/11.11
See application file for complete search history.

(56) References Cited

U.S. PATENT DOCUMENTS

| 2,127,903 | A | 3/1938 | Bowen |
| 4,511,653 | A | 4/1985 | Play et al. |
| 4,902,508 | A | 2/1990 | Badylak et al. |
| 4,956,178 | A | 9/1990 | Badylak et al. |
| 4,981,465 | A | 1/1991 | Ballan |

(Continued)

FOREIGN PATENT DOCUMENTS

| EP | 1570788 | 9/2005 |
| EP | 1671591 | 6/2006 |

(Continued)

OTHER PUBLICATIONS

Himpson, Rebecca C. et al., "Histological evidence for enhanced anal fistula repair using autologous fibroblasts in a dermal collagen matrix," Comparative Clinical Pathology, Apr. 2006, vol. 16, No. 1.

(Continued)

*Primary Examiner* — Vy Q Bui
(74) *Attorney, Agent, or Firm* — Woodard, Emhardt, Moriarty, McNett & Henry LLP

(57) ABSTRACT

This invention provides, in certain aspects, unique devices and methods for treating fistulae. In one embodiment, an inventive device includes an elongate graft body having a proximal end and a distal end. The graft body is configurable to a first condition and a second condition, the second condition including the distal end deflected laterally relative to its position in the first condition of the body. The device also includes a tether, which is connected to the graft body, and is configured to traverse proximally along the body. The tether is manipulable to convert the graft body from the first condition to the second condition. Such a device may also include one or more additional tethers connected to the graft body. For instance, a second tether can be configured to extend distally from the distal end of the graft body, and may be effective in pulling the graft body along a fistula tract.

30 Claims, 7 Drawing Sheets

(56) References Cited

U.S. PATENT DOCUMENTS

| | | | |
|---|---|---|---|
| 5,061,274 | A | 10/1991 | Kensey |
| 5,192,302 | A | 3/1993 | Kensey et al. |
| 5,222,970 | A | 6/1993 | Reeves |
| 5,275,826 | A | 1/1994 | Badylak et al. |
| 5,281,422 | A | 1/1994 | Badylak et al. |
| 5,304,123 | A | 4/1994 | Atala et al. |
| 5,334,216 | A | 8/1994 | Vidal |
| 5,374,261 | A | 12/1994 | Yoon |
| RE34,866 | E | 2/1995 | Kensey |
| RE34,977 | E | 2/1995 | Kensey et al. |
| 5,411,475 | A | 5/1995 | Atala et al. |
| 5,516,533 | A | 5/1996 | Badylak et al. |
| 5,554,389 | A | 9/1996 | Badylak et al. |
| 5,584,827 | A | 12/1996 | Korteweg et al. |
| 5,620,461 | A | 4/1997 | Muijs Van De Moer |
| 5,628,762 | A | 5/1997 | Al-Tameem |
| 5,643,305 | A | 7/1997 | Al-Tameem |
| 5,752,974 | A | 5/1998 | Rhee et al. |
| 5,755,791 | A | 5/1998 | Whitson et al. |
| 5,779,672 | A | 7/1998 | Dormandy |
| 5,830,228 | A | 11/1998 | Knapp et al. |
| 5,955,110 | A | 9/1999 | Patel et al. |
| 5,993,844 | A | 11/1999 | Abraham et al. |
| 5,997,575 | A | 12/1999 | Whitson et al. |
| 6,090,996 | A | 7/2000 | Li |
| 6,099,567 | A | 8/2000 | Badylak et al. |
| 6,126,686 | A | 10/2000 | Badylak et al. |
| 6,206,931 | B1 | 3/2001 | Cook et al. |
| 6,220,336 | B1 | 3/2001 | Badylak et al. |
| 6,315,787 | B1 | 11/2001 | Tsugita |
| 6,375,989 | B1 | 4/2002 | Badylak et al. |
| 6,569,081 | B1 | 5/2003 | Nielsen et al. |
| 6,666,892 | B2 | 12/2003 | Hiles et al. |
| 2003/0013989 | A1 | 1/2003 | Obermiller et al. |
| 2003/0051735 | A1 | 3/2003 | Pavcnik et al. |
| 2004/0158185 | A1 | 8/2004 | Moran et al. |
| 2004/0176798 | A1 | 9/2004 | Epstein et al. |
| 2005/0013844 | A1 | 1/2005 | Hadlock et al. |
| 2005/0049626 | A1 | 3/2005 | Burgard |
| 2005/0070759 | A1 | 3/2005 | Armstrong |
| 2005/0155608 | A1 | 7/2005 | Pavcnik et al. |
| 2005/0159776 | A1 | 7/2005 | Armstrong |
| 2005/0182495 | A1 | 8/2005 | Perrone |
| 2006/0004408 | A1 | 1/2006 | Morris et al. |
| 2006/0015142 | A1 | 1/2006 | Malazgirt |
| 2006/0074447 | A2 | 4/2006 | Armstrong |
| 2007/0031508 | A1 | 2/2007 | Armstrong et al. |
| 2008/0004657 | A1* | 1/2008 | Obermiller et al. ........... 606/213 |

FOREIGN PATENT DOCUMENTS

| | | |
|---|---|---|
| RU | 2180529 | 3/2002 |
| SU | 1673130 | 11/1991 |
| SU | 1718837 | 3/1992 |
| WO | WO 93/07813 | 4/1993 |
| WO | WO 98/25637 | 6/1998 |
| WO | WO 00/19912 | 4/2000 |
| WO | WO 00/72759 | 12/2000 |
| WO | WO 2004/012627 | 2/2004 |
| WO | WO 2005/020823 | 3/2005 |
| WO | WO 2005/020847 | 3/2005 |
| WO | WO 2005/070302 | 8/2005 |
| WO | WO 2006/119256 | 11/2006 |
| WO | WO 2007/002260 | 1/2007 |
| WO | WO 2007/011443 | 1/2007 |
| WO | WO 2007/064819 | 6/2007 |
| WO | WO 2007/090150 | 8/2007 |
| WO | WO 2007/090155 | 8/2007 |

OTHER PUBLICATIONS

Khairy, G.E.A., et al., "Percutaneous obliteration of duodenal fistula," J.R. Coll. Surg. Edinb., 45 Oct. 2000, 342-344.

Lisle, David A., et al., "Percutaneous Gelfoam Embolization of Chronic Enterocutaneous Fistulas: Report of Three Cases," Diseases of the Colon & Rectum, vol. 50, No. 2, Dec. 2006.

Maluf-Fiho, F., et al., "Endoscopic Treatment of Esophagogastric Fistulae with an Acellular Matrix," Gastrointestinal Endoscopy, Elsevier, NL, vol. 59, No. 5, Apr. 2004, p. 151, XP004854594 abstract.

Miklos, J.R., et al., "Rectovaginal Fistula Repair Utilizing a Cadaveric Dermal Allograft," International Urogynecology Journal, 1999, vol. 10, No. 6, pp. 405-406.

Moore, Robert D., et al., "Rectovaginal Fistula Repair Using a Porcine Dermal Graft," Obstetrics & Gynecology, 2004, 104, 1165-1167.

Schultz, David J., et al., "Porcine Small Intestine Submucosa as a Treatment for Enterocutaneous Fistulas," Journal of American Collage of Surgeons, 2002, vol. 194, No. 4, Apr. 2002, pp. 541-543.

Schwesinger, Wayne H., "Management of Persistent Fistula After Gastrectomy", on-line question (www.medscape.com), posted on May 14, 2002.

Shah, A.M., et al., "Bronchoscopic closure of bronchopleural fistula using gelfoam," Abstract, Journal of Association of Physicians of India, 2004, vol. 52, n JUIN, pp. 508-509.

Shaker MA, et al., "Competent Closure of Chronic Oroantral Fistula with Zenoderm," Egypt Dent J. Jul. 1995; 41(3):1237-42.

Sheiman, Robert G. et al., "Percutaneous Treatment of a Pancreatic Fistula after Pancreaticoduodenectomy," J Vasc Intery Radiol, 2001, vol. 12, No. 4, pp. 524-526.

Shelton, Andrew A., et al., Transperineal Repair of Persistent Rectovaginal Fistulas Using an Acellular Cadaveric Dermal Grant (AlloDerm®). Diseases of the Colon & rectum, Sep. 2006, vol. 49, No. 9.

Wilson Gunn on behalf of unnamed party, Letter to the European Patent Office, Jan. 30, 2007, pp. 1-4.

* cited by examiner

FISTULA GRAFTS HAVING A DEFLECTABLE GRAFT BODY PORTION

REFERENCE TO RELATED APPLICATION

The present application claims the benefit of U.S. Provisional Patent Application Ser. No. 60/947,573 filed Jul. 2, 2007, entitled FISTULA GRAFTS HAVING A DEFLECTABLE GRAFT BODY PORTION which is hereby incorporated by reference in its entirety.

BACKGROUND

The present invention relates generally to medical devices and in particular aspects to grafts useful in treating fistulae.

As further background, a variety of fistulae can occur in humans, and they can occur for a variety of reasons including but not limited to, as a congenital defect, as a result of inflammatory bowel disease, such as Chron's disease, irradiation, trauma, such as childbirth, or as a side effect from a surgical procedure. Further, several different types of fistulae can occur, for example, urethro-vaginal fistulae, vesico-vaginal fistulae, tracheo-esophageal fistulae, enterocutaneous fistulae including gastro-cutaneous fistulae, and any number of anorectal fistulae, such as recto-vaginal fistula, recto-vesical fistulae, recto-urethral fistulae, or recto-prostatic fistulae.

Anorectal fistulae can result from infection in the anal glands, which are located around the circumference of the distal anal canal that forms the anatomic landmark known as the dentate line. Approximately 20-40 such glands are found in humans. Infection in an anal gland can result in an abscess. This abscess then can track through soft tissues (e.g., through or around the sphincter muscles) into the perianal skin, where it drains either spontaneously or surgically. The resulting void through soft tissue is known as a fistula. The internal or inner opening of the fistula, usually located at or near the dentate line, is known as the primary opening. Any external or outer openings, which are usually located in the perianal skin, are known as secondary openings. The path which these fistulae take, and their complexity, can vary. A fistula may take a take a "straight line" path from the primary to the secondary opening, known as a simple fistula. Alternatively, the fistula may consist of multiple tracts ramifying from the primary opening and have multiple secondary openings. This is known as a complex fistula.

A gastrointestinal fistula is an abnormal passage that leaks contents of the stomach or the intestine (small or large bowel) to other organs, usually other parts of the intestine or the skin. For example, gastrojejunocolic fistulae include both enterocutaneous fistulae (those occurring between the skin surface and the intestine, namely the duodenum, the jejunum, and the ileum) and gastric fistulae (those occurring between the stomach and skin surface). Another type of fistula occurring in the gastrointestinal tract is an enteroenteral fistula, which refers to a fistula occurring between two parts of the intestine. Gastrointestinal fistulae can result in malnutrition and dehydration depending on their location in the gastrointestinal tract. They can also be a source of skin problems and infection. The majority of these types of fistulae are the result of surgery (e.g., bowel surgery), although sometimes they can develop spontaneously or from trauma, especially penetrating traumas such as stab wounds or gunshot wounds. Inflammatory processes, such as infection or inflammatory bowel disease (Crohn's disease), may also cause gastrointestinal fistulae. In fact, Crohn's disease is the most common primary bowel disease leading to enterocutaneous fistulae, and surgical treatment may be difficult because additional enterocutaneous fistulae develop in many of these patients postoperatively.

Surgical treatment of fistulae can involve passing a fistula probe through a fistula tract in a blind manner, using primarily only tactile sensation and experience to guide to probe. Having passed the probe through the fistula tract, the overlying tissue is surgically divided. This is known as a fistulotomy. In treating certain types of fistulae, e.g., perianal fistulae, a fistulotomy may result in impaired sphincter control, and even frank incontinence, since varying amounts of sphincter muscle may be divided during the procedure.

There remain needs for improved and/or alternative devices and methods for treating fistulae. The present invention is addressed to those needs.

SUMMARY

The present invention provides, in certain aspects, unique devices for treating fistulae. One such device comprises an elongate graft body including a proximal end, a distal end and an intermediate portion occurring therebetween. The intermediate portion includes an inner passage extending from a first exterior sidewall surface to a second exterior sidewall surface. The graft body is configurable to a first condition and a second condition. The second condition includes the distal end deflected laterally relative to its position in the first condition of the graft body. This device further comprises a tether connected to the graft body distally of the inner passage. The tether is configured to traverse proximally along the graft body and extend through the inner passage. The tether is manipulable to convert the body from the first condition to the second condition, and may be a suture strand or other similar object. The elongate graft body may be formed with one or more of a variety of biocompatible materials including some that are naturally derived and some that are non-naturally derived. In a preferred embodiment, the graft body is comprised of a remodelable, angiogenic material, for example, a remodelable extracellular matrix material such as submucosa.

In another aspect, the invention provides a method of treating a fistula having at least a first fistula opening, a second fistula opening, and a fistula tract extending therebetween. This method includes providing a fistula graft device comprised of an elongate graft body and a tether. The elongate graft body has a proximal end and a distal end. The graft body is configurable to a first condition and a second condition. The second condition includes the distal end deflected laterally relative to its position in the first condition of the graft body. The tether is connected to the graft body, and is configured to traverse proximally along the graft body. The tether is manipulable to convert the graft body from the first condition to the second condition. In one method step, the graft body is positioned in the fistula tract, wherein a distal portion of the graft body including the distal end extends a distance out from the first fistula opening. In another step, the tether is manipulated to convert the graft body from the first condition to the second condition. The graft body is then maintained generally in the second condition with at least a portion of the graft body positioned in the fistula tract. A variety of fistulae may be treated according to this and other inventive methods In one embodiment, such a method is adapted to treat a fistula having a first fistula opening in a bladder wall and a second fistula opening in a vaginal wall.

Another aspect of the invention provides a fistula graft device comprising an elongate graft body, a first tether and a second tether. The graft body has a proximal end and a distal end, and is configurable to a first condition and a second condition. The second condition includes the distal end deflected laterally relative to its position in the first condition of the graft body. The first tether is connected to the graft body, and is configured to traverse proximally along the graft body. The first tether is manipulable to convert the graft body from the first condition to the second condition. The second tether is connected to the graft body, and is configured to extend distally from the distal end of the graft body. The second tether is effective in pulling the graft body in a fistula tract. In one embodiment, a single suture strand provides the first tether and the second tether.

Other objects, embodiments, forms, features, advantages, aspects, and benefits of the present invention shall become apparent from the detailed description and drawings included herein.

DETAILED DESCRIPTION

Figure 1:
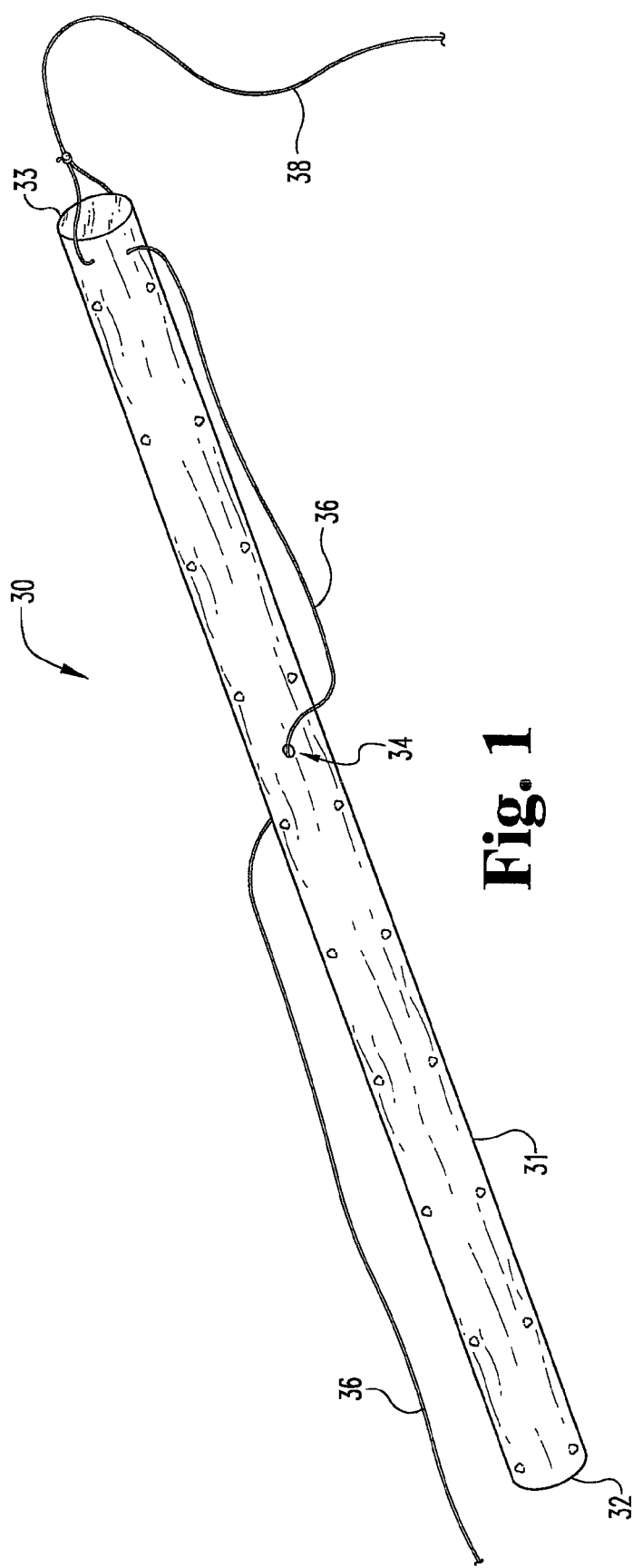
FIG. 1 is a perspective view of a fistula graft device according to one embodiment of the present invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique devices and methods for treating fistulae. In general, an inventive device will include an elongate graft body having a distal end that can be deflected in some manner through manipulation of the device. Illustratively, a graft body may be configurable to a first condition and a second condition, wherein the second condition includes the distal end deflected laterally relative to its position in the first condition of the graft body. In a first condition, second condition or any other condition, a graft body useful in the invention can exhibit a variety of shapes and configurations. In some cases, a graft body, when in a first condition, will permit passage of the distal end through a fistula tract and a distance out from a fistula opening. Then, the graft body can be converted to and maintained generally in a second condition, wherein passage of the distal end back through the fistula opening, or at least back through all or part of the fistula tract, is inhibited. When the graft body is in such a second condition, the position of its distal end relative to other portions of the graft body can vary. In some instances, the distal end will contact a portion of the graft body that is located proximally of the distal end. As well, when the graft body is in such a second condition, its position in the fistula (and relative to any nearby bodily structures) can vary. Illustratively, the distal end of the graft body, when deflected, may reside in and/or around the fistula opening, and in some instances, will reside wholly or partially in the fistula tract. Additionally or alternatively, the distal end, when deflected, may contact portions of the bodily structure wall in which the fistula opening occurs.

The invention provides a variety of device designs permitting a distal end of an elongate graft body to be deflected in some manner through manipulation of the device. In some cases, an inventive device incorporates a tether, cord or other similar object, which is attached to otherwise suitably associated with an elongate graft body, and is manipulable to convert the graft body from a first condition to a second condition. Preferably, this second condition includes a distal end of the graft body laterally deflected relative to its position in the first condition of the graft body. Devices of this sort can vary widely with regard to how these components are shaped and configured, as well as to the manner in which they are arranged.

Illustratively, such a device can include a thin, elongate object (e.g., a suture strand) affixed to the distal end of the elongate graft body and traversing proximally along the graft body. In one mode of converting the graft body, a portion of the body including its proximal end is held in a generally stationary position, while the suture strand is pulled in a direction generally away from the distal end of the graft body. Sufficient pulling will be effective to deflect the distal end of the graft body relative to its position in the graft body prior to this pulling. In traversing proximally along the graft body, the suture strand may pass through a volume of the graft body, and in some cases, through more than one such volume. For example, the suture strand may pass through an inner passage extending from a first exterior surface to a second exterior surface of the graft body. An inner passage of this sort may be generally straight, or alternatively, it may be curved or bent in some fashion or otherwise suitably shaped to enable a desirable deflection of the graft body distal end to occur.

The orientation of an inner passage in a graft body can vary. In certain aspects, an inner passage will extend between two exterior sidewall surfaces of a graft body. Illustratively, a straight or somewhat curved inner passage may extend between two such surfaces in an area of an elongate graft body located between its longitudinal midpoint and its distal end. In instances where a graft body has a central longitudinal axis, an inner passage may extend through this region, or alternatively, may extend through a portion of the graft body excluding this axis. In a preferred embodiment, an inner passage (e.g., one that is generally straight) will extend diametrically through a generally cylindrical plug body volume. As well, an inner passage may be perpendicular to or somewhat angled relative to a central longitudinal axis of a graft body. For instance, a generally straight inner passage may be angled to some extent toward either end of an elongate graft body.

Turning now to a more detailed discussion of materials useful in the invention, graft bodies such as graft body 31 may be formed with one or more of a variety of materials including some that are naturally derived and some that are non-naturally derived. In advantageous embodiments, these devices are comprised of a remodelable material. Particular advantage can be provided by graft devices including a remodelable collagenous material. Such remodelable collagenous materials, whether reconstituted or non-reconstituted, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or within tissue in which a graft device of the invention is implanted, e.g., around tissue defining a fistula tract, an opening to a fistula, or another space in the body.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Graft devices of the invention can include xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

ECM materials used in the invention may be essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Turning now to a discussion of drying techniques that can be useful in certain embodiments of the invention, drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. The amount of void space or open matrix structure within an ECM material that has been dried by evaporation is typically more diminished than, for example, an ECM material dried by lyophilization as described below.

A suitable lyophilization process can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a separately performed pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure, that is characteristic of the harvested ECM material.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

In certain aspects, the invention provides graft devices that include a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the device while simultaneously employing the vacuum to press the device together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

As well, graft devices of the invention may be comprised of biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Graft devices of the invention can also include a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly (lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

Graft bodies useful in the invention can have a variety of shapes. In some forms, a graft body will include an elongate portion having an essentially constant cross-sectional area along its length. Additionally or alternatively, a graft body may include an elongate portion having a varying cross-sectional area along its length, for example, one that tapers in a linear or curvilinear fashion. In this regard, all or a portion of an elongate graft body may be generally cylindrical, conical or conical-like, or otherwise suitably shaped for use in accordance with the present invention. Although not necessary to broader aspects of the invention, in certain embodiments, a single unitary construct provides an elongate graft body in an inventive device. In other embodiments, two or more individual graft body constructs are connected together or otherwise joined to provide a suitable elongate graft body.

The dimensions of a graft body can vary as well. For instance, while a graft body can have any suitable length for use in treating a fistula in accordance with the present invention, in general, a graft body will have a length of at least about 1 cm, and in many instances at least about 3 cm to about 20 cm (approximately 1 to 8 inches). In some preferred embodiments, a graft body will have a length ranging from about 6 cm to about 15 cm (approximately 2 to 6 inches). Suitable graft body lengths will be recognized by those skilled in the art, and therefore, are encompassed by the present invention. In some instances, the length of a graft body is altered before, during and/or after engraftment in a patient. Illustratively, a graft body having excess length can be provided, and this length can be reduced after the graft body is implanted, for example, a proximal portion of a graft body extending from a fistula opening can be trimmed off after the graft body is fixed in place at the treatment site. Additionally, in instances where an elongate graft body portion is considered to have a diameter, the size of this diameter can vary, and may or may not be constant along the length of this portion. At any point along the length of such a graft body portion, the diameter can range from about 0.1 mm to about 25 mm, or more typically from about 5 mm to about 15 mm. In certain forms, a generally conical portion is tapered along its length so that one end of the portion has a diameter of about 5 mm to about 15 mm, while the opposite end of the portion has a diameter of about 0.5 mm to about 5 mm. Such a taper may or may not be continuous along the length of the portion, and may have linear and/or curvilinear characteristics.

The graft bodies described herein can be formed in a variety of manners including some that involve extrusion, using a mold or form, construction around a mandrel, and/or combinations or variations thereof. In some embodiments, a graft body is formed with a reconstituted or otherwise reassembled ECM material. Graft bodies can also be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, a graft body is constructed by randomly or regularly packing one or more pieces of single or multilayer ECM sheet material within a mold and thereafter processing the packed material. Graft bodies useful in the invention can be prepared, for example, as described in International Patent Application Serial No. PCT/US2006/16748, filed Apr. 29, 2006, and entitled "VOLUMETRIC GRAFTS FOR TREATMENT OF FISTULAE AND RELATED METHODS AND SYSTEMS" (Cook Biotech Incorporated), which is hereby incorporated by reference in its entirety.

Methods for forming graft bodies useful in the invention can involve manipulating a material within a mold or form. It should be noted that this material may or may not be hydrated when placed in, on, around, etc. the mold or form. In some methods, a substantially dry ECM material (e.g., a powder or sheet material) can be placed in a mold and then suitably hydrated for further processing. In other methods, a hydrated starting material is placed in and/or on a mold or forming structure for further processing. For example, one or more hydrated sheets of ECM material can be applied to a form, e.g., wrapped at least partially around a mandrel so that portions of the sheet(s) overlap. Then, the one or more sheets can be dried, and in some embodiments, dried while under compression, to form a unitary graft construct.

In some modes of operation, a hydrated graft material is provided within a single- or multiple-part mold having a plurality of apertures or holes extending through a wall of the mold, thereby providing access to the mold interior from an external location. These apertures can serve to enhance drying of a hydrated material during a processing step and in processes exerting vacuum pressure at these apertures, can promote and/or facilitate formation of surface protuberances on the graft material as portions of the same are drawn toward the apertures while under vacuum. In one aspect, an amount of ECM material is retained in such a mold, and needles or other material-displacing objects are inserted through some or all of the mold apertures and a distance into the ECM material, thereby displacing volumes of the ECM material. This can be performed when the graft material is hydrated, partially hydrated or dehydrated. In some forms, with needles inserted in a hydrated ECM material and providing passages therein, the material is subjected to conditions (e.g., freezing and/or dehydrating conditions) which, alone or in combination with one or more other conditions, cause or allow the passages to be generally retained in the ECM material after the needles are removed.

In one embodiment, one or more sheets of hydrated ECM material are suitably wrapped and/or randomly packed around a mandrel, and then a mold having a plurality of holes extending through a wall of the mold is placed around the material-covered mandrel, for example, so that an amount of pressure is placed on the ECM material. The mandrel can then optionally be removed. Thereafter, needles or other material-displacing objects are inserted through some or all of the holes and at least partially through the ECM material, thereby displacing volumes of the ECM material. The ECM material is then at least partially dried. In some aspects, a suitable lyophilization technique is employed, e.g., one with or without a pre-freezing step as described herein. In these or other drying methods in which needles or other penetrating elements are to be left within the mass during drying, these elements can optionally be provided with a plurality of apertures or holes or can otherwise be sufficiently porous to facilitate the drying operation by allowing the passage of hydrate from the wet mass. In one embodiment, a hydrated ECM material with emplaced needles can be subjected to freezing conditions so that the material and any contained hydrate become substantially frozen. Thereafter, the needles can be removed from the ECM material, and the remaining construct (with the frozen material passages substantially retaining their shape) can be placed under a vacuum so that the frozen hydrant sublimes from the material, thereby resulting in a dry graft construct with retained passages therein.

In other modes of operation, passage-forming structures can be incorporated integrally into a mold so that passageways are formed upon introducing the starting material in and/or on the mold. In these aspects, the passage-forming structures can be part of the mold (e.g., extend from a surface of the mold), or they can be separate objects attached or otherwise coupled to the mold, to provide the desired passage or passages through the ultimately-formed graft body.

Although not necessary to broader aspects of the invention, in some aspects, the formation of such a graft construct comprises wrapping one or more sheets of hydrated graft material around a mandrel a number of times. The resulting roll of graft material is then introduced into a mold, and the mandrel is removed (optional), e.g., before or after applying the mold. Thereafter, multiple material-displacing objects such as but not limited to needles are forced through apertures in the mold and into the hydrated graft material, and the material is subjected to one or more drying techniques such as a lyophilization process. In other aspects, the formation of such a graft construct includes placing a flowable graft material into a mold and then subjecting the graft material to further processing. For example, a flowable ECM material mass, such as a gel, paste or putty, potentially incorporating a particulate ECM material, can be placed into a mold, and then with volumes of material displaced in the mass (e.g., by penetrating needles), the ECM material can be dried or otherwise caused to form an integral piece to provide a graft body having passages therein. Illustratively, each of the passages can be provided by forcing a single object through the material mass, or alternatively, where a mandrel is left in place to form a longitudinal lumen, by forcing two objects into the mass and toward one another from opposite directions until they abut the mandrel. The mass can then be processed to a solid graft body as discussed herein.

Some inventive devices include an elongate graft body having a generally cylindrical shape. With reference now to FIG. 1, shown is a fistula graft device 30 according to one embodiment of the present invention. Device 30 includes a generally cylindrical, elongate graft body 31 having a proximal end 32 and a distal end 33. An inner passage 34 extends through the graft body in an area of the graft body that is located approximately midway between the proximal and distal ends. Device 30 also includes a first tether 36, which is connected to the graft body, and is configured to traverse proximally along the graft body. As shown in FIG. 1, first tether 36 may be passed through inner passage 34, and can be configured to extend proximally of proximal end 32. Device 30 additionally includes a second tether 38, which is connected to the graft body, and is configured to extend distally from the distal end of the graft body. These and other tethers useful in the invention can be formed with a variety of materials, and in some instances, will be formed with a resorbable material such as 2-0 vicryl material.

The present invention provides a variety of methods for treating fistulae. In general, an inventive method will include positioning an elongate graft body in a fistula tract such that a distal end of the graft body extends a distance out from a first fistula opening. In certain embodiments, positioning the graft body in the fistula tract in this manner includes advancing the distal end of the graft body through a second fistula opening, through the fistula tract, and out of the first fistula opening. Thereafter, the distal end is deflected in some manner through manipulation of the device, and the graft body is generally maintained in this condition with at least a portion of the graft body positioned in the fistula tract. When secured in place at the treatment site, the graft body may fill all or a portion of the fistula tract. Additionally, the graft body may block, and in some cases seal off, the first fistula opening.

Figure 2:
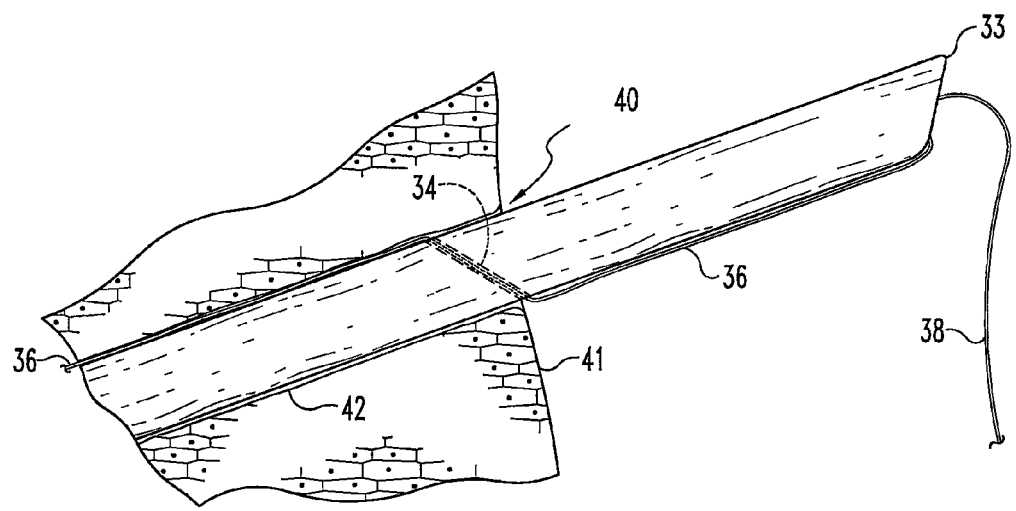
FIG. 2 shows an elongate graft body of an inventive device positioned in a fistula tract.

Referring now to FIG. 2, shown is a partial, side view of an inventive device positioned in a fistula having a first fistula opening 40 in a wall 41 of a bodily structure, and a fistula tract 42 extending from this opening. This device is similar to that shown in FIG. 1 except that the distal end 33 of the graft body is somewhat tapered. Having a tapered end is optional, and thus, while a tapered end may be useful in certain embodiments of the invention, it will be understood that a graft body distal end useful in the invention, whether tapered or non-tapered, can exhibit a variety of shapes and configurations. In cases where a graft body distal end is able to contact another portion of the graft body when sufficiently deflected, the distal end may be particularly shaped and adapted to enhance such contact. Selecting a particular distal end shape can also take into account the manner in which the distal end contacts bodily structures at the treatment site in instances where such contact is to occur. Illustratively, a graft body distal end can be designed to enhance its ability to reside in and around, and in some cases become lodged within, a fistula opening when converted to and maintained in a deflected condition.

Continuing with FIG. 2, the graft body can be so positioned by advancing distal end 33 through a second fistula opening (not shown), through the fistula tract, and a distance out from fistula opening 40. This distance may be varied as desired to suit a particular application, device, etc. Thus, while the distance shown in FIG. 2 may be useful in certain embodiments of the invention, it is not intended to limit any aspect of the present invention. In such a position, second tether 38 is essentially free to hang from the graft body, while first tether 36 traverses along the graft body and passes into the fistula tract. Advantageously, first tether 36 will be sufficiently long to extend through the fistula tract and a distance out from the second fistula opening when the graft body is in a position to be converted.

First tether 36 passes through inner passage 34 as it traverses along the graft body. Inner passage 34 extends diametrically through a portion of the generally cylindrical graft body at an angle of approximately 45° relative to the graft body's central longitudinal axis. While this location in the graft body may be useful in certain embodiments of the invention, it will be understood that an inner passage of this sort may be positioned in a variety of locations in a graft body. Those skilled in the art will recognize suitable locations, and therefore, these locations are encompassed by the present invention. Illustratively, in instances where an elongate graft body portion is considered to have a central longitudinal axis, a generally straight inner passage, whether extending diametrically through the graft body portion or whether offset from its diameter in some fashion, may occur at any suitable angle relative to the central longitudinal axis. In some aspects, such an inner passage will be generally perpendicular to the central longitudinal axis of a graft body portion. In other aspects, an inner passage will extend at an angle relative to a graft body portion's central longitudinal axis, for example, from about 1° to about 30° toward either end of the graft body portion.

A graft body useful in the invention such as that shown in FIG. 2 can be advanced through a fistula tract in a variety of manners including some that involve pushing and/or pulling the body through the tract, whether by hand, using instruments, or both. In one embodiment, the distal end of the graft body (with second tether 38 out in front) is forced through a second fistula opening, at least part of the way through the fistula tract, and potentially out of a first fistula opening by hand. Additionally or alternatively, second tether 38 can be grasped (e.g., with a suitable instrument) and used to pull the graft body in some manner through the fistula. Once the graft body is desirably positioned in the fistula tract, for example as shown in FIG. 2, converting it to a condition that includes its distal end laterally deflected in some manner includes pulling first tether 36 through the fistula tract in a direction generally away from the first fistula opening. The extent of deflection can be varied. Once the distal end is desirably deflected, the graft body can be generally maintained in this condition.

Inventive devices and methods may be used to treat a variety of fistulae including at least some of those having (i) a fistula opening in a bladder wall or other bladder-related bodily structure wall (e.g., in a wall of the urethra, a ureter wall, a prostate gland wall, etc.); and (ii) a fistula tract extending therefrom. These include but are not limited to recto-vesical fistulae, recto-urethral fistulae, recto-prostatic fistulae, urethra-vaginal fistulae and vesico-vaginal fistulae.

In instances involving the treatment of female patients, inventive devices and methods may be adapted to treat fistulae having (i) a fistula opening in a vaginal or uterine canal wall; (ii) and a fistula tract extending therefrom. These include but are not limited to enterovaginal fistulae such as recto-vaginal fistulae, urethra-vaginal fistulae and vesico-vaginal fistulae. In one method of use, the distal end of the graft body (with second tether 38 out in front) is forced by hand through a vaginal wall fistula opening, at least part of the way through a fistula tract, and potentially out of a bladder wall fistula opening and a distance into the bladder. Additionally or alternatively, second tether 38 can be grasped with a suitable grasping instrument and used to pull the graft body in some manner through the fistula. The graft body is advanced until it is desirably positioned in the fistula tract, for example, with the graft body distal end extending a distance into the bladder and the graft body inner passage positioned at or near the bladder wall fistula opening. With the proximal end of the first tether 36 extending from the vaginal wall fistula opening, it is grasped and pulled generally away from the vaginal wall fistula opening to convert the graft body to a condition that includes the distal end of the graft body laterally deflected in some manner. In doing so, it may be necessary and/or desirable to hold the graft body steady in the fistula tract as it is being converted, for example, by applying back pressure to a portion of the body including its proximal end. In some cases, impingement of the graft body by tissues surrounding the fistula may be enough to hold the body steady as it is being converted. Once the converted graft body is desirably positioned at the treatment site, it can be generally maintained in this condition to provide treatment.

In certain embodiments, a cytoscope or other similar device is employed to desirably position a graft body in a fistula tract, e.g., a fistula tract extending between the bladder and the vaginal canal. In general, these devices will be equipped to directly or indirectly grasp or otherwise maintain contact with the graft body in an effort to advance the graft body in the fistula tract. In doing so, these devices can be delivered to a variety of locations in the body for becoming associated with the graft device (e.g., a graft body, tether, etc.). Illustratively, the distal end of a cytoscope can be inserted into the urethra and advanced until it enters the bladder. In instances where part of the graft device (e.g., a tether) has been delivered into the bladder, the cytoscope can grasp or otherwise connect to this part of the graft device in the bladder. Thereafter, the cytoscope can be manipulated to desirably position the graft body in the fistula tract, for example, by withdrawing the cytoscope back through the urethra to pull the distal end of the graft body through the fistula tract and into the bladder. The cytoscope can then be disassociated from the graft device.

In other instances, the distal end of a cytoscope or other similar device will be delivered into the bladder, and thereafter, advanced through a bladder-side fistula opening, through a fistula tract, and through a vaginal-side fistula opening (and into the vaginal canal). The cytoscope and a graft device can then be joined, and the graft body can be pulled into the fistula tract by withdrawing the cytoscope back through the fistula tract. Withdrawal of the cytoscope can be continued until the graft body is desirably positioned, and then the cytoscope can be disassociated from the graft device.

Regardless of the location in the body at which a cytoscope or other similar device is joined to a graft device, there are a variety of manners in which the two may be united including some that involve using one or more hooks, fasteners, straps, suture strands, and other single- and multiple-part coupling devices and/or materials effective to bond or otherwise hold the devices together. Suitable means for joining a graft device and a delivery instrument will be recognized by those skilled in the art, and therefore, are encompassed by the present invention. In some instances, a graft device and a delivery device are able to maintain contact with one another through the use of magnetic force, and thus, both devices may be equipped accordingly. Inventive methods and systems involving the use of magnetic force may be particularly useful in instances where part of a graft device (e.g., a graft body, tether, etc.) is to be located and retrieved in a less accessible area of the body such as in the bladder. Any suitable magnetic materials may be used in this regard including rare-earth magnets.

Figure 3:
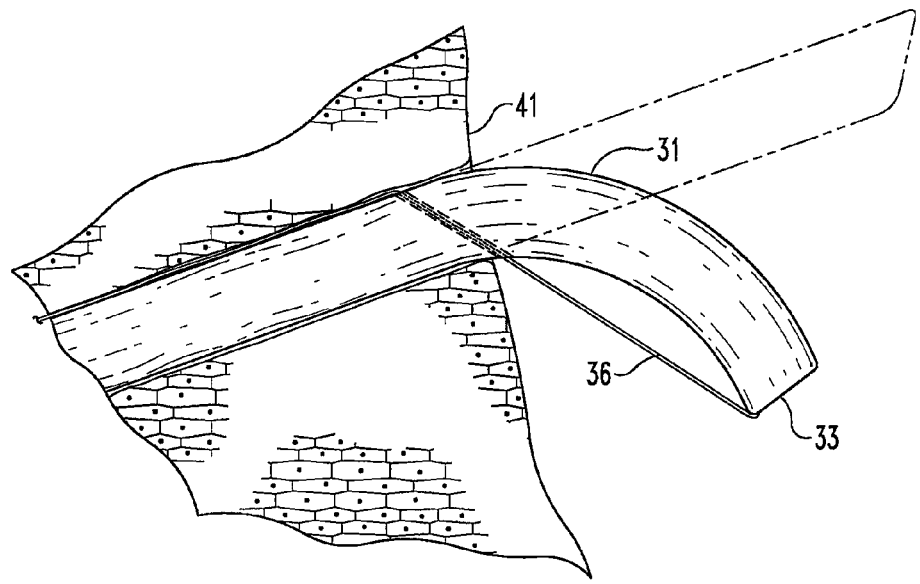
FIG. 3 shows the graft body of FIG. 2 in a condition that includes its distal end laterally deflected relative its position in FIG. 2.

With reference now to FIG. 3, shown is the fistula graft device of FIG. 2 converted to a condition that includes the distal end of the graft body somewhat deflected. This condition is one of many to which a graft body of this sort can be configured. In some instances, what is shown will be considered a full conversion, and the graft body will be generally maintained in this condition (and in this position in the fistula) for providing treatment. In other instances, different graft body shaping and/or positioning of the converted graft body at the treatment site will be achieved, for example, by deflecting the distal end of the graft body to a greater or lesser extent, altering the position of the graft body in the fistula tract and in and/or around a fistula opening, etc.

Once the graft body is desirably shaped and positioned in the body, steps can be taken to maintain the graft body in this condition and at a general location in the body to provide treatment. Illustratively, first tether 36 can be sewn, bonded or otherwise affixed to the graft body so that the distal end remains deflected in a desirable fashion. Additionally or alternatively, first tether 36 can be affixed to patient tissue in the area of treatment, for example, tied off to tissue at the second fistula opening. Desirable placement of the graft body can also involve suturing or otherwise securing the graft body to such tissues. In some cases, impingement of the graft body by tissues at the treatment site (e.g., tissue lining the fistula tract) will be at least partially responsible for maintaining the graft body in a desirable configuration and/or at a desirable location in the body to provide treatment. For instance, in one embodiment, a graft body will be situated at a fistula treatment site with its deflected distal end pulled back a distance into the fistula tract. In this arrangement, a portion of the graft body including its distal end will be in contact with another portion of the graft body at a location proximal of the distal end, wherein these combined portions will fit rather snugly in the fistula tract, and in some cases, become sufficiently lodged within the fistula tract to generally maintain the graft body in this configuration in the fistula tract. Yet, even in such instances, the graft body can still be affixed to patient tissue in the area of treatment, for example, tied off to tissue at the second fistula opening.

Figure 4:
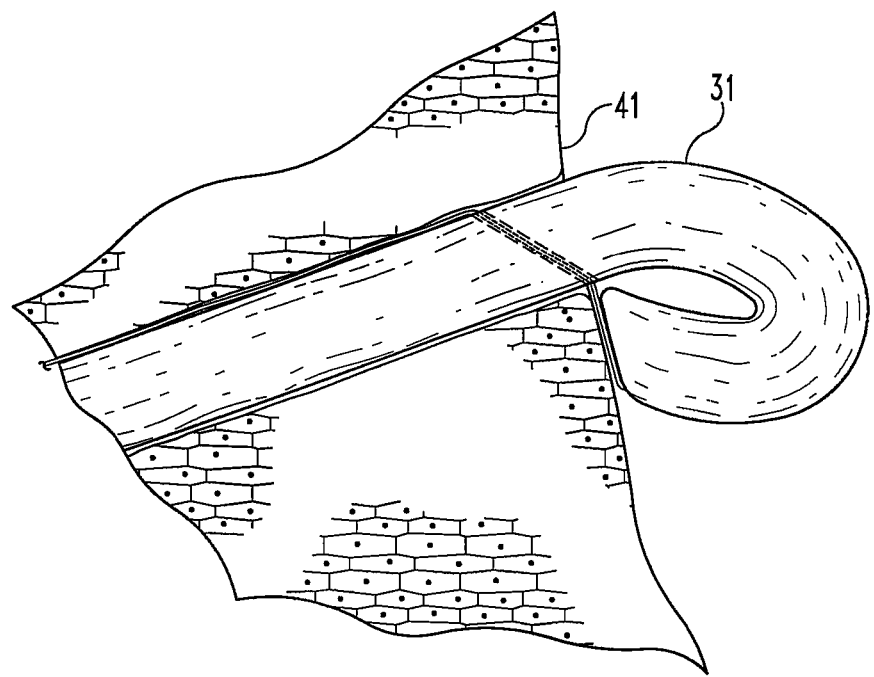
FIG. 4 shows the graft body of FIG. 2 in another condition that includes its distal end laterally deflected relative its position in FIG. 2.

Referring now to FIG. 4, shown is the fistula graft device of FIG. 2 converted to a condition that includes the distal end of the graft body somewhat deflected. In this condition, the distal end of the graft body is pulled closer to bodily structure wall 41 compared to the graft body configuration shown in FIG. 2. Also, the distal end is pulled closer to other portions of the graft body occurring proximal of the distal end. Again, the graft body can be generally maintained in such a condition (and in such a position in the fistula) for providing treatment. In alternative embodiments, however, the graft body can be differently shaped and/or positioned in the body for providing treatment as described elsewhere herein.

Figure 5:
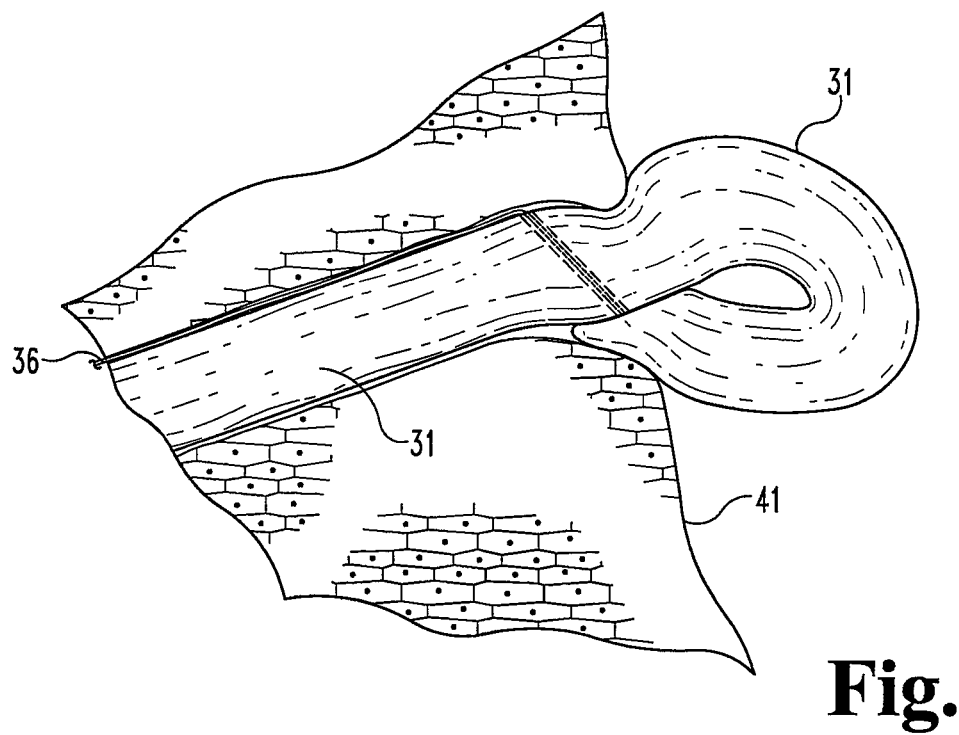
FIG. 5 shows the graft body of FIG. 2 in yet another condition that includes its distal end laterally deflected relative its position in FIG. 2.

With reference now to FIG. 5, shown is the fistula graft device of FIG. 2 converted to a condition that includes the distal end of the graft body somewhat deflected. In this condition, the graft body distal end is in contact with another, more proximal portion of the graft body, and these "combined" portions are positioned in and around the first fistula opening. In some cases, the graft body will be positioned in the fistula tract so that this sort of arrangement is achieved upon pulling first tether 36. In other cases, the combined portions will be located generally outside and away from the fistula opening upon converting the graft body. Then, the combined portions are pulled back a distance into the fistula tract, for example, as shown in FIG. 5. Illustratively, the graft body can be converted, and then while holding the first tether steady relative to the graft body, the proximal end of the graft body can be grasped and used to pull the converted graft body back a distance through the fistula tract. In some cases, combined graft body portions will become firmly lodged within the fistula tract.

Additionally, a graft body such as that shown in FIG. 5 may incorporate one or more adaptations to facilitate and/or otherwise enhance its conversion from a first condition to a second condition. Illustratively, a graft body may have indentations, scores, thinner portions, and/or other similar adaptations in one or more areas along the graft body. These and other adaptations for enhancing conversion of a graft body from a first condition to a second condition will be recognized by the skilled artisan and are therefore encompassed by the present invention.

Figure 6:
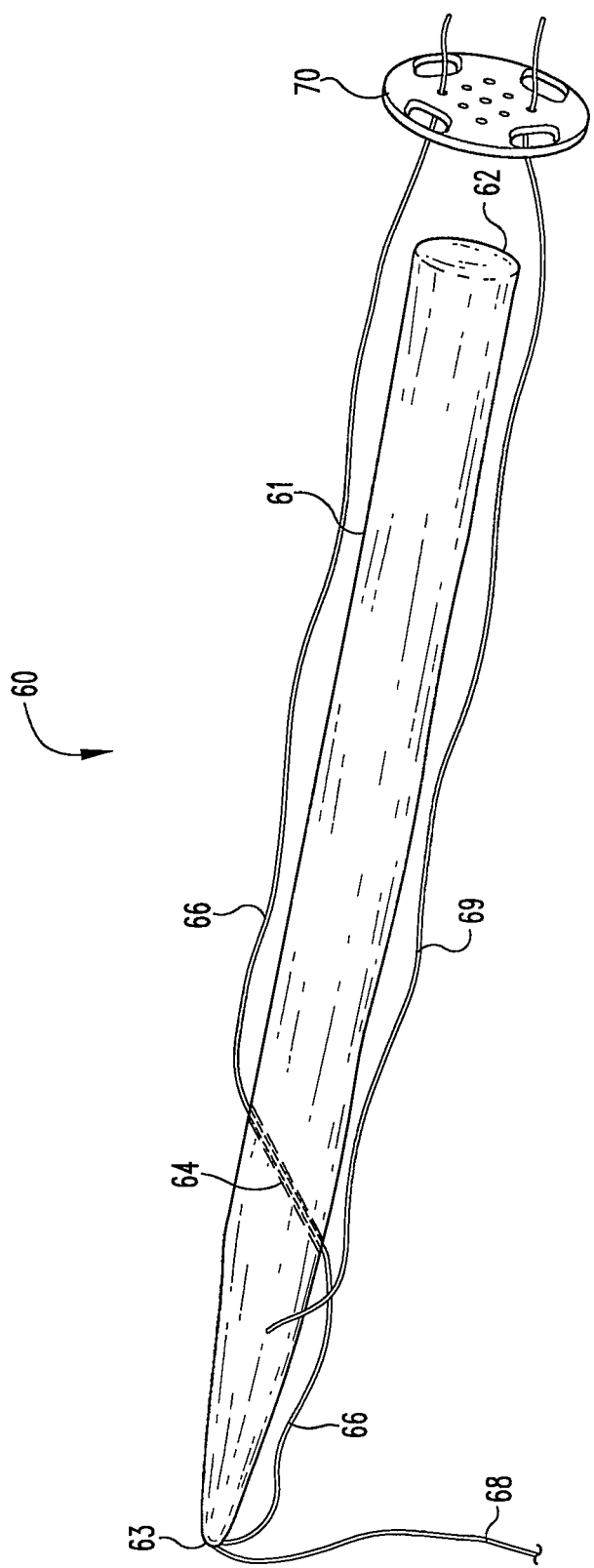
FIG. 6 is a perspective view of a fistula graft device according to another embodiment of the present invention.

With reference now to FIG. 6, shown is a fistula graft device 60 according to another embodiment of the present invention. Device 60 includes an elongate graft body 61 having a proximal end 62 and a distal end 63. A substantial longitudinal segment of graft body 61 including its proximal end 62 is generally cylindrical. Extending from this cylindrical portion is a tapered portion culminating in distal end 63. Approximately where the graft body begins to taper, an inner passage 64 extends through the graft body, although other suitable orientations may be utilized as described elsewhere herein. Device 60 also includes a first tether 66, which is connected to the graft body, and is configured to traverse proximally along the graft body. As shown in FIG. 6, first tether 66 may be passed through inner passage 64, and can be configured to extend proximally of proximal end 62. Device 60 additionally includes a second tether 68, which is connected to the graft body, and is configured to extend distally from the distal end of the graft body. A third tether 69 is connected to the graft body, and is configured to traverse proximally along the graft body. First tether 66 and third tether 69 can both be passed through an optional disc-shaped capping member 70.

In one method of use, an inventive device such as device 60 is used to treat a fistula having a fistula opening in a bladder wall, another fistula opening in a vaginal canal wall, and a fistula tract extending therebetween. Illustratively, the distal end of a cytoscope or other similar device is inserted into the urethra and advanced until it enters the bladder. Thereafter, this distal end is advanced through the bladder-side fistula opening, through the fistula tract, and through the vaginal-side fistula opening (and into the vaginal canal). The cytoscope is manipulated to releasably grasp second tether 68. Thereafter, the cytoscope is withdrawn back through the fistula tract, pulling graft body 61 therealong. The graft body is advanced in this manner until it is desirably positioned in the fistula tract, for example, with inner passage 64 positioned at or near the bladder-side fistula opening and distal end 63 extending a distance into the bladder. Second tether 68 can then be released and the cytoscope withdrawn entirely from the body. Then, with the proximal end of the first tether 66 extending from the vaginal wall fistula opening, the graft body is "held steady" in the fistula tract, for example, by gripping and holding the graft body at the vaginal-side opening. The first tether 66 is then pulled generally away from the vaginal-side opening to convert the graft body to a condition that includes the distal end of the graft body laterally deflected in a desirable manner. Once the distal end is desirably deflected (e.g., with the deflected distal end alongside another portion of the graft body and pulled back a distance through the fistula tract), the graft body can be generally maintained in this condition to provide treatment. Any excess portion of the graft body extending from the vaginal-side opening may then be trimmed off. In embodiments including capping member 70, this capping member can be advanced over first tether 66 and third tether 69 until it contacts the graft body, and then can be affixed to the graft body and/or patient tissue at the vaginal-side opening. Passages in the capping member will allow for drainage from the fistula tract to pass through the capping member and out into the vaginal canal.

Figure 7A:
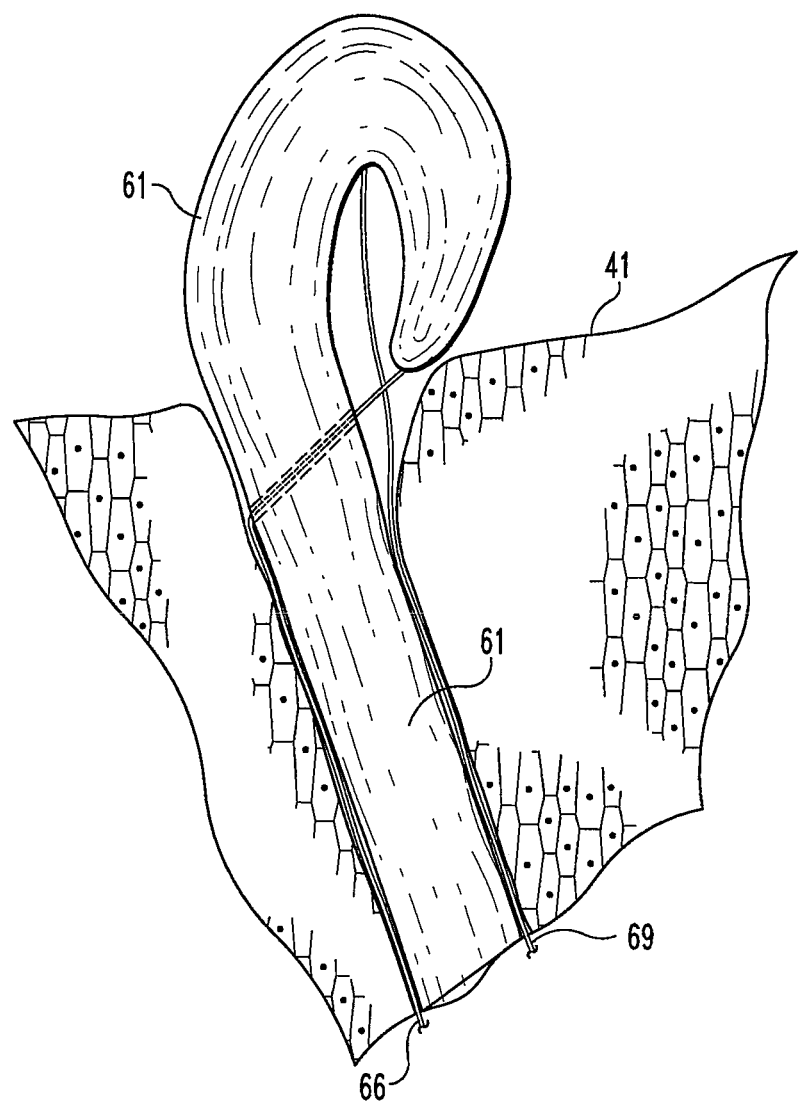
FIG. 7A shows a fistula graft device according to yet another embodiment of the present invention and a step in one illustrative inventive method.
Figure 7B:
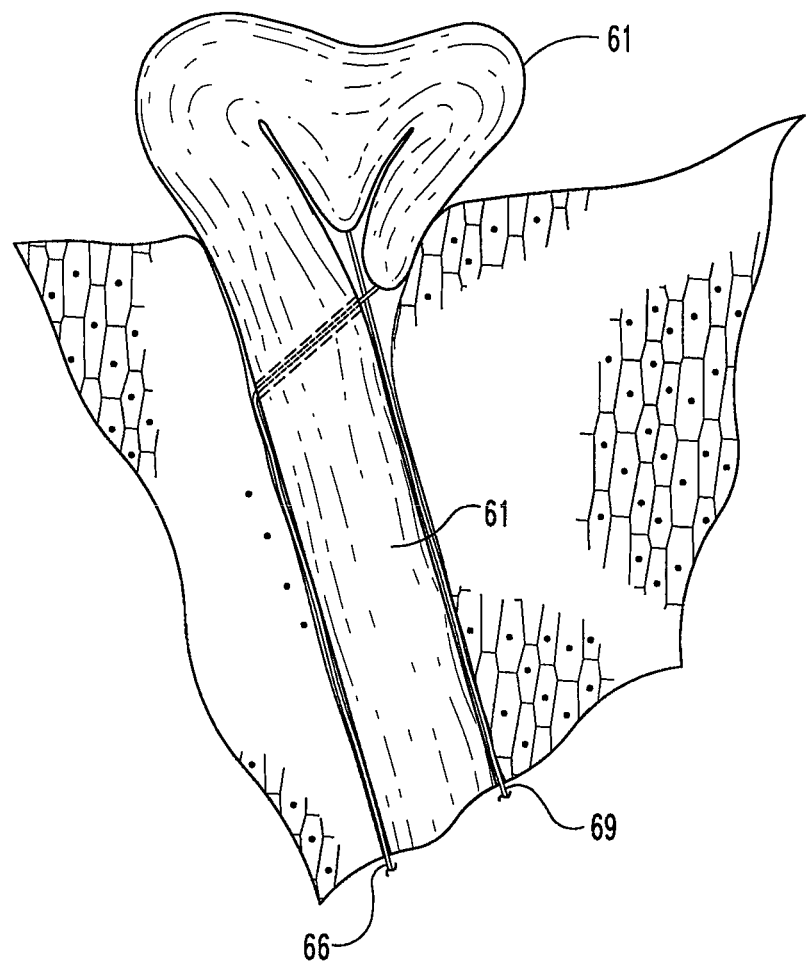
FIG. 7B shows the device of FIG. 7B in a different configuration at the treatment site.

As discussed elsewhere herein, tethers and other pullable members can serve a variety of functions in an inventive device. In some instances, third tether 69, in addition to perhaps being used to maintain the shape and/or positioning of the graft device at the treatment site, can also be used to modify the shape of the graft device in the body. FIG. 7A shows a step in one specific illustrative inventive method in which first tether 66 is being used to convert graft body 61 to a condition that includes the distal end of the graft body somewhat laterally deflected. FIG. 7B shows another step in which third tether 69 is being used to further modify distal regions of the plug. With the first tether pulled such that the distal end of the plug is drawn toward the fistula opening, third tether 69 is pulled proximally through the fistula tract such that portions of the graft body to which third tether 69 is attached are pulled therealong toward (and potentially into) the first fistula opening 40. Once desirably modified, the graft body can be generally maintained in this condition to provide treatment.

While FIGS. 7A and 7B illustrate a useful inventive device and steps that can be taken to modify the shape of that device in the body, various other devices and device modifications are contemplated as within the scope of the present invention. An inventive device can incorporate any suitable number of tethers, and a tether can be attached to or otherwise associated with a graft body in any suitable manner. No matter the number of tethers incorporated into an inventive device, the positioning of a tether relative to the graft body and relative to any other tether that might be present in the device can be varied, for example, to allow a particular type of modification to be achieved. Also, the degree to which a tether is pulled can be varied to effect a desired modification. Thus, when an inventive device incorporates a first and third tether such as those depicted in FIGS. 7A and 7B, either tether can be pulled to a greater or lesser extent than what is shown. As well, the sequence in which multiple tethers are manipulated can be varied depending on the type of modification desired. Manipulations of this sort can enhance the graft's ability to block the opening, and in some cases, to substantially seal off the opening (e.g., to exclude the fistula from the bladder, etc.), for example, by packing graft material more tightly into the fistula opening or otherwise increasing the density of the graft material in regions in and/or around the fistula opening. Such manipulations may also be effective to increase the surface area of graft material in regions in and/or around the fistula opening.

Capping members such as capping member 70, when utilized in the present invention, can exhibit a variety of shapes and sizes. In general, a capping member will be configured to cap a fistula opening occurring in a bodily structure wall, and in some instances to firmly contact portions of the bodily structure wall adjacent to the opening. A capping member and an elongate graft body may be formed separately and then attached to one another or otherwise suitably united, or alternatively, the two may be formed as a single unit, for example, from a single piece of material. When formed separately, the two members may be united, for example, using an adhesive, by suturing, using mechanical fastener(s), and/or employing any other suitable joining means. A capping member may be formed with one or more of a variety of materials including some that are naturally derived and some that are non-naturally derived. These include a variety of metallic and synthetic polymeric materials.

A capping member can include one or more objects (e.g., devices, pieces of material, etc.) that, together or alone, exhibit a three-dimensional rectilinear or curvilinear shape. Suitable three-dimensional rectilinear shapes can have any suitable number of sides, and can include, for example, cubes, cuboids, tetrahedrons, prisms, pyramids, wedges, and variations thereof. Suitable three-dimensional curvilinear bodies can include, for example, spheres, spheroids, ellipsoids, cylinders, cones, and any suitable variations thereof (e.g., a segment of a sphere, or a truncated cone, etc.). Capping members useful in the invention can be prepared, for example, as described in International Patent Application Serial No. PCT/US2006/024260, filed Jun. 21, 2006, and entitled "IMPLANTABLE GRAFT TO CLOSE A FISTULA" (Cook Biotech Incorporated); and U.S. Provisional Patent Application Ser. No. 60/763,521, filed Jan. 31, 2006, and entitled "FISTULA GRAFTS AND RELATED METHODS AND SYSTEMS FOR TREATING FISTULAE" (Cook Biotech Incorporated), which are hereby incorporated by reference in their entirety. In some preferred embodiments, a capping member and/or a graft body comprise a remodelable, angiogenic material, for example, a remodelable extracellular matrix material such as submucosa.

In some forms, a graft device and/or a device being used in its delivery includes a radiopaque element such as but not limited to a radiopaque coating, attached radiopaque object, or integrated radiopaque substance for monitoring the movement of the object through the body during a delivery procedure. In this regard, any suitable radiopaque substance, including but not limited to, tantalum such as tantalum powder, can be incorporated into such inventive devices. Other radiopaque markers may be comprised of bismuth, iodine, and barium, as well as other suitable radiopaque materials.

Figure 8:
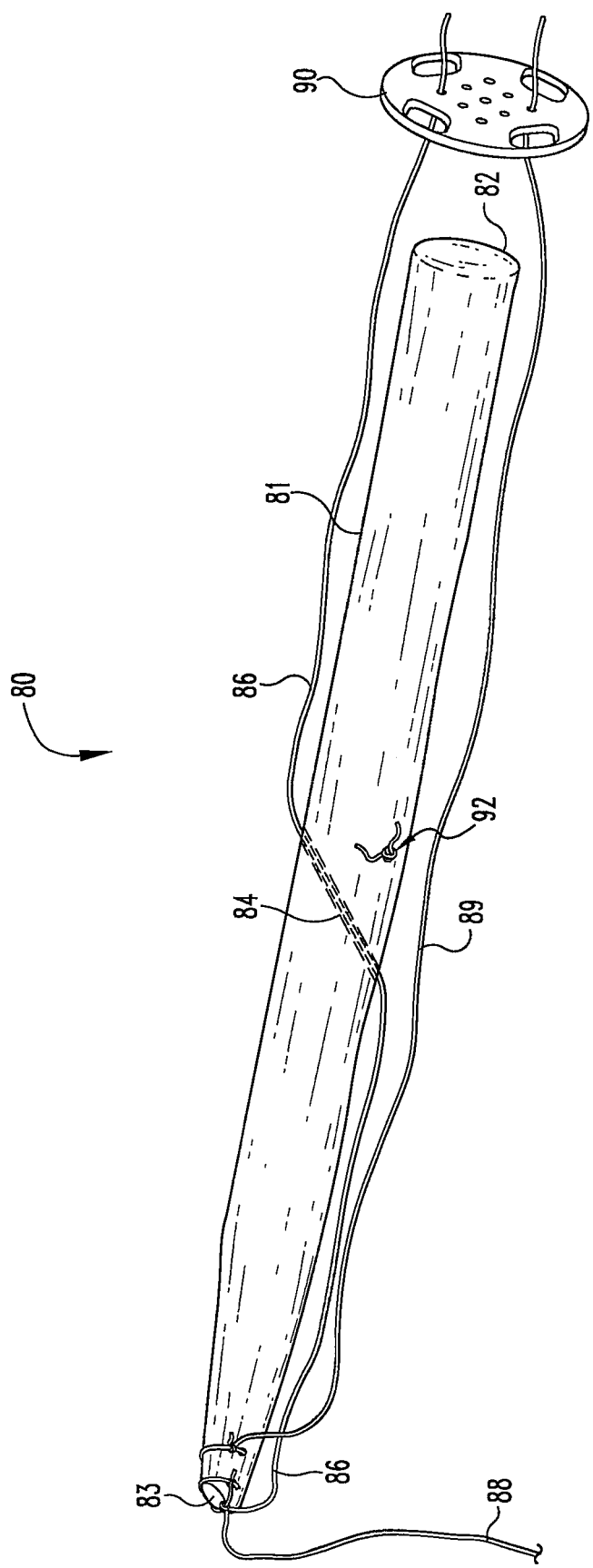
FIG. 8 is a perspective view of a fistula graft device according to another embodiment of the present invention.

FIG. 8 shows a fistula graft device 80 according to another embodiment of the present invention. Device 80 includes an elongate graft body 81 having a proximal end 82. A majority of graft body 81 is generally cylindrical. Toward more distal regions of the plug, the graft body narrows, culminating in a narrowed, distal end 83. An inner passage 84 extends through the graft body at a location slightly distal of the midpoint of the plug, although passages of this sort can occur at other locations in the graft body as discussed elsewhere herein. Device 80 also includes a first tether 86, which is connected to the graft body, and is configured to traverse proximally along the graft body. Illustratively, first tether 86 can be tied through and around portions of the graft body, e.g., by being passed through a passage occurring in the graft body. As shown in FIG. 8, first tether 86 can be passed through inner passage 84, and can extend proximally of proximal end 82. Device 80 additionally includes a second tether 88, which is tied through and around portions of the graft body, and can extend distally from the distal end of the graft body. In some instances, a tether such as second tether 88 may be an extension of another tether. A third tether 89 is connected to the graft body, and can extend proximally from the graft body. First tether 86 and third tether 89 can both be passed through an optional disc-shaped capping member 90.

Although not necessary to broader aspects of the invention, in one specific illustrative embodiment, device 80 is used in much the same way as described above in relation to FIG. 6 to treat a fistula having a fistula opening in a bladder wall, another fistula opening in a vaginal canal wall, and a fistula tract extending therebetween. Thus, a cytoscope or other suitable instrument extending through the vaginal-side fistula opening (and into the vaginal canal) can be used to releasably grasp second tether 88. Thereafter, the cytoscope is withdrawn back through the fistula tract, pulling graft body 81 therealong. The graft body is advanced in this manner until it is desirably positioned in the fistula tract. To facilitate this positioning, device 80 includes a radiopaque suture 92. Device 80 and other inventive devices can incorporate one or more radiopaque sutures or other suitable markers at various locations on the device. Markers of this sort can allow the practitioner to determine the orientation of a device part relative to another device part in the body and/or to determine the location of that device part relative to structures or spaces in the body (e.g., its proximity to a fistula opening) from outside the body. Thus, graft body 81 can be advanced until suture 92 is positioned at or near the bladder-side fistula opening, with distal end 83 extending into the bladder. Then, with the proximal end of the first tether 86 extending from the vaginal wall fistula opening, the graft body is "held steady" in the fistula tract, for example, by gripping and holding the graft body at the vaginal-side opening. The first tether 86 (and optionally also the third tether 89) is then pulled generally away from the vaginal-side opening to convert the graft body to a condition that includes the distal end of the graft body somewhat laterally deflected. Once the distal end is desirably modified (e.g., with distal portions of the plug folded over one another and packed into the fistula opening), the graft body can be generally maintained in this condition to provide treatment. Capping member 90 can be advanced over first tether 86 and third tether 89 until it contacts the graft body and/or tissue adjacent the fistula tract, and then can be affixed to the graft body and/or patient tissue at the vaginal-side opening.

There are a variety of ways to shape and configure the distal regions of an inventive plug such that upon conversion of the plug at the treatment site, the converted plug exhibits a desirable shape and configuration for blocking, and in some cases substantially sealing off, a fistula opening or passage through which the plug extends. The shape and configuration chosen for the distal regions of a particular inventive plug may depend, for example, on how those distal regions will interact with other plug portions and/or other structures at the treatment site (e.g., tissue in and/or around a fistula opening) once the plug is converted. In some instances, this at least means that the plug will have a narrowed distal region similar to that shown in FIG. 8, although plugs having bulging, protruding, or other suitably shaped distal regions are contemplated as well. When an inventive device includes a narrowing distal region, such a region can take a variety of forms. A narrowing portion can have rectilinear and/or curvilinear features. A narrowing portion may taper or otherwise narrow along a longitudinal section of the plug in a uniform fashion, or it may taper or otherwise narrow in a non-uniform fashion. In the specific illustrative embodiment of FIG. 8, an additional taper occurs at distal end 83 resulting in a distal surface having a generally elliptical shape. Forming the distal end into this and other useful shapes can enhance the converted plug's ability to plug the fistula and otherwise provide treatment upon conversion. Various elliptical and non-elliptical shapes may be utilized in this regard. Distal regions of a plug can display rectilinear and/or curvilinear features. Inventive devices, in some forms, will include a distal portion adapted to fit into and/or around another plug portion (e.g., a more proximal portion) upon conversion of the plug. Cooperation of plug portions in this manner can be in a generally controlled fashion; e.g. wherein one portion of the plug engages another portion in a fashion that is predictably controlled by engaged surface features of the two portions.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A fistula graft device, comprising:
   an elongate graft body including a proximal end, a distal end and an intermediate portion occurring therebetween, the intermediate portion including an inner passage extending laterally through the graft body from a first exterior sidewall surface to a second exterior sidewall surface, the graft body configurable to a first condition and a second condition, the second condition including the distal end deflected laterally relative to its position in the first condition of the graft body; and
   a first tether connected to the graft body at a connection point distal to the inner passage, the tether traversing proximally along the graft body from said connection point and passing through the inner passage,
   wherein the tether is manipulable to convert the graft body from the first condition to the second condition.

2. The fistula graft device of claim 1, further comprising a second tether connected to the graft body, the second tether configured to extend distally from the distal end of the graft body and effective in pulling the graft body in a fistula tract.

3. The fistula graft device of claim 1, wherein the first tether is connected to the graft body at the distal end of the graft body.

4. The fistula graft device of claim 1, wherein the elongate graft body includes a generally cylindrical portion.

5. The fistula graft device of claim 1, wherein the elongate graft body includes a tapered portion.

6. The fistula graft device of claim 1, wherein the elongate graft body includes a narrowing region occurring distally of the proximal end.

7. The fistula graft device of claim 1, wherein a single unitary construct provides the proximal end, distal end and intermediate portion of the elongate graft body.

8. The fistula graft device of claim 1, wherein the elongate graft body includes a rolled sheet material providing a volumetric body.

9. The fistula graft device of claim 8, wherein the rolled sheet material provides spiral layers.

10. The fistula graft device of claim 9, wherein the spiral layers are compressed and bonded so as to form a substantially unitary construct.

11. The fistula graft device of claim 1, wherein the elongate graft body comprises a synthetic polymeric material.

12. The fistula graft device of claim 1, wherein the elongate graft body comprises a collagenous material.

13. The fistula graft device of claim 1, wherein the elongate graft body comprises a remodelable material.

14. The fistula graft device of claim 1, wherein the elongate graft body comprises an extracellular matrix material.

15. The fistula graft device of claim 14, wherein the extracellular matrix material comprises serosa, pericardium, dura mater, peritoneum, or dermal collagen.

16. The fistula graft device of claim 1, wherein the second condition further includes the distal end of the graft body contacting another portion of the graft body at a location proximal of the distal end.

17. A method of treating a fistula having at least a first fistula opening, a second fistula opening, and a fistula tract extending therebetween, the method comprising:
    positioning the graft body of a fistula graft device according to claim 1 in the fistula tract, wherein a distal portion of the graft body including the distal end extends a distance out from the first fistula opening; and
    manipulating the first tether to convert the graft body from the first condition to the second condition.

18. The method of claim 17, wherein the first fistula opening occurs in a bladder wall, and the second fistula opening occurs in a vaginal wall.

19. The method of claim 17, wherein said positioning includes advancing the graft body through the fistula tract in a delivery device lumen.

20. The method of claim 17, wherein said positioning includes pushing the distal end of the graft body through the second fistula opening, through the fistula tract, and out of the first fistula opening.

21. The method of claim 17, wherein said positioning includes pulling the graft body through the fistula tract and toward the first fistula opening.

22. The method of claim 17, wherein the fistula graft device includes a second tether, the second tether connected to the graft body and configured to extend distally from the distal end of the graft body, and wherein said positioning includes pulling the graft body through the fistula tract and toward the first fistula opening with the second tether.

23. The method of claim 17, wherein said manipulating includes pulling the tether so that the tether advances in the fistula tract in a direction from the first fistula opening and toward the second fistula opening.

24. The method of claim 17, wherein the first fistula opening occurs in a bodily structure wall, and wherein the graft body is maintained generally in the second condition with portions of the graft body contacting portions of the bodily structure wall adjacent the first fistula opening.

25. The method of claim 17, wherein the second condition further includes the distal end of the graft body contacting another portion of the graft body at a location proximal of the distal end.

26. A fistula graft device, comprising:
    an elongate graft body having a proximal end and a distal end, the graft body configurable to a first condition and a second condition, the second condition including the distal end deflected laterally relative to its position in the first condition of the graft body;
    a first tether connected to the graft body and configured to traverse proximally along the graft body, the first tether manipulable to convert the graft body from the first condition to the second condition;
    a second tether connected to the graft body and configured to extend distally from the distal end of the graft body, the second tether effective in pulling the graft body in a fistula tract; and
    wherein said elongate graft body includes an inner passage extending laterally through the graft body, and wherein said first tether is connected to the graft body at a connection point distal of the inner passage, said first tether traversing proximally along the graft body from said connection point and passing through said inner passage.

27. The fistula graft device of claim 26, wherein a single suture strand provides the first tether and the second tether.

28. The fistula graft device of claim 26, wherein said inner passage is generally perpendicular to a central longitudinal axis of the elongate graft body.

29. The fistula graft device of claim 26, wherein said inner passage is at a 45 degree angle relative to a central longitudinal axis of the elongate graft body.

30. The fistula graft device of claim 26, wherein said inner passage enters the graft body through a first exterior sidewall surface and exits the graft body through a second exterior sidewall surface.

* * * * *